(12) United States Patent
Johnson et al.

(10) Patent No.: US 11,179,573 B2
(45) Date of Patent: Nov. 23, 2021

(54) PHOTOBIOMODULATION THERAPY FOR URINARY INCONTINENCE

(71) Applicant: MULTI RADIANCE MEDICAL, Solon, OH (US)

(72) Inventors: Douglas Johnson, Brownstown, MI (US); Max Kanarsky, Solon, OH (US); Ernesto Cesar Pinto Leal-Junior, Sao Paulo (BR)

(73) Assignee: MULTI RADIANCE MEDICAL, Solon, OH (US)

( * ) Notice: Subject to any disclaimer, the term of this patent is extended or adjusted under 35 U.S.C. 154(b) by 0 days.

(21) Appl. No.: 17/202,998

(22) Filed: Mar. 16, 2021

(65) Prior Publication Data

US 2021/0268303 A1    Sep. 2, 2021

Related U.S. Application Data

(63) Continuation-in-part of application No. PCT/US2019/051414, filed on Sep. 17, 2019.

(60) Provisional application No. 62/732,185, filed on Sep. 17, 2018.

(51) Int. Cl.
  *A61N 5/06*  (2006.01)
  *A61N 2/00*  (2006.01)
  *A61N 2/06*  (2006.01)

(52) U.S. Cl.
  CPC .......... *A61N 5/0613* (2013.01); *A61N 2/002* (2013.01); *A61N 2/006* (2013.01); *A61N 2/06* (2013.01); *A61N 2005/0643* (2013.01); *A61N 2005/0659* (2013.01); *A61N 2005/0663* (2013.01)

(58) Field of Classification Search
  None
  See application file for complete search history.

(56) References Cited

U.S. PATENT DOCUMENTS

| | | |
|---|---|---|
| 2003/0011455 A1 | 1/2003 | Wakuda |
| 2011/0184500 A1 | 7/2011 | Reil |
| 2016/0317833 A1 | 11/2016 | Tedford et al. |
| 2017/0106201 A1* | 4/2017 | Schwarz .............. A61N 5/0625 |
| 2017/0128736 A1 | 5/2017 | Johnson et al. |

OTHER PUBLICATIONS

International Search Report and Written Opinion dated Dec. 4, 2019 for Application No. PCT/US2019/051414.

\* cited by examiner

*Primary Examiner* — Ankit D Tejani
(74) *Attorney, Agent, or Firm* — Tarolli, Sundheim, Covell & Tummino LLP

(57) ABSTRACT

Photobiomodulation therapy (PBMT) provides an effective, non-invasive treatment for urinary incontinence that can be used discretely. A light source device can be contacted to a subject's skin proximal to a subject's bladder. A light signal can be applied in at least one of a pulsed operating mode, a continuous operating mode, and a super-pulsed operating mode through the light source device to the subject's skin proximal to the subject's bladder. The light signal can be applied for a time sufficient to stimulate a phototherapeutic response in one or more muscles and/or nerves proximal to the bladder to treat urinary incontinence.

15 Claims, 6 Drawing Sheets

PHOTOBIOMODULATION THERAPY FOR URINARY INCONTINENCE

CROSS-REFERENCE TO RELATED APPLICATIONS

This application is a Continuation in Part of Intl Patent Application No. PCT/US19/51414, filed Sep. 17, 2019, entitled "PHOTOBIOMODULATION THERAPY FOR URINARY INCONTINENCE", which claims the benefit of U.S. Provisional Application No. 62/732,185, filed Sep. 17, 2018, entitled "PHOTOBIOMODULATIONTHERAPY FOR URINARY INCONTINENCE". The entirety of these applications is hereby incorporated by reference for all purposes.

TECHNICAL FIELD

The present disclosure relates generally to urinary incontinence and, more specifically, to systems and methods that treat urinary incontinence with photobiomodulation therapy.

BACKGROUND

Urinary incontinence is the involuntary leakage of urine from the bladder. This involuntary leakage is a common and distressing problem, which may have a large impact on quality of life. In fact, many patients suffering from urinary incontinence suffer from embarrassment or fear, leading to urinary incontinence being underreported to medical practitioners. While exercise training techniques like pelvic floor muscle training and bladder training are somewhat effective at treating the involuntary leakage, the exercise techniques do not work for every patient and, even in patients who do see a benefit, the benefit is to a varying degree. More effective treatments, like surgery and electrical stimulation, are invasive and painful.

SUMMARY

The present disclosure relates to systems and methods treat urinary incontinence with photobiomodulation therapy (PBMT) by increasing strength of muscles proximal to the bladder (e.g., to increase strength of pelvic floor muscles and/or bladder muscles) and/or improving conduction of neurons innervating the bladder and/or the bladder sphincter. PBMT provides an effective, non-invasive treatment for urinary incontinence that can be used discretely. Additionally, PBMT can be used in combination with exercise techniques (and/or other non-invasive therapies) to increase effectiveness.

According to an aspect, a method for using PBMT to treat urinary incontinence is described. A light source device can be contacted to a subject's skin proximal to a subject's bladder (e.g., near one or more muscles and/or nerves related to function of the subject's bladder and/or bladder sphincter). A light signal can be generated by the light source device and applied in at least one of a pulsed operating mode, a continuous operating mode, and a super-pulsed operating mode through the light source device to the subject's skin proximal to the subject's bladder. The light signal is applied for a time sufficient to stimulate a phototherapeutic response in one or more muscles proximal to the bladder to treat urinary incontinence (e.g., by strengthening the one or more muscles).

According to another aspect, a system that uses PBMT to treat urinary incontinence is described. The system includes at least three light sources each configured to apply a portion of the light signal comprising a different wavelength within a wavelength range of 600-1100 nm through the light source device to the subject's skin proximal to the subject's bladder. Each of the at least three light sources operates in a pulsed operating mode, a continuous operating mode, or a super-pulsed operating mode. The system also includes a processing unit preprogrammed with a time of application of the first pulsed light, the second pulsed light, and the third light signal. The time of application is sufficient to stimulate a phototherapeutic response in one or more muscles proximal to the bladder to treat urinary incontinence. The system further includes a power source (e.g., one or more batteries and/or a line power source).

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
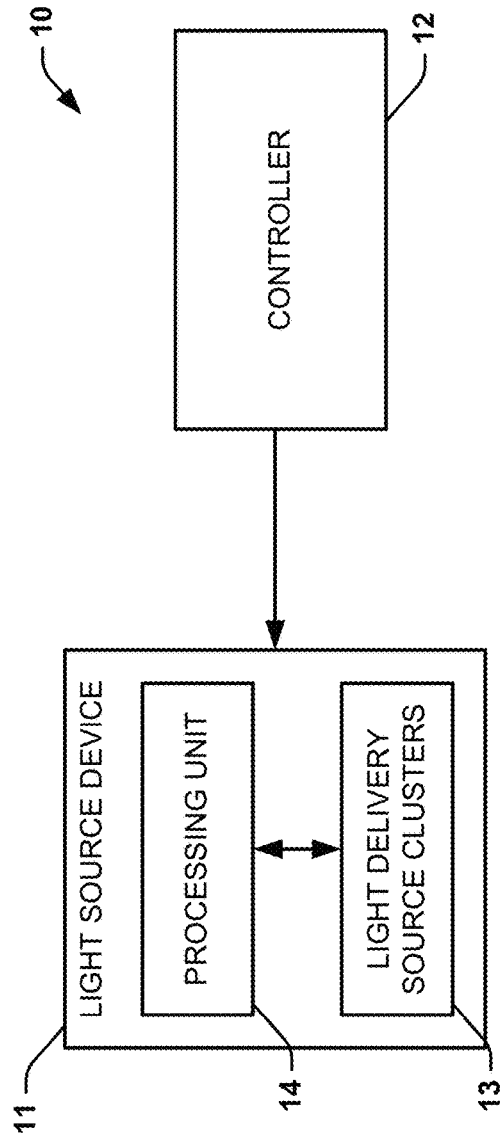
FIG. 1 is a block diagram illustration showing an example of a system that configures and applies a photobiomodulation therapy (PBMT) to an area proximal to a subject's bladder in accordance with an aspect of the present disclosure.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

As used herein, the term "urinary incontinence" can refer to the loss of bladder control characterized by involuntary leakage of urine. Examples of urinary incontinence can include urge incontinence and stress incontinence.

As used herein, the term "urge incontinence" can refer to a type of urinary incontinence characterized by a sudden and strong need to urinate. Urge incontinence can be due to an unstable detrusor muscle and/or an overactive bladder.

As used herein, the term "stress incontinence" can refer to a type of urinary incontinence that is due to poor closure of the bladder sphincter. Stress incontinence happens, for example, when physical movement or activity puts pressure (stress) on the bladder.

As used herein, the term "photobiomodulation" refers to the application of a light signal to a portion of a subject's body to induce a phototherapeutic response in cells within the portion of the subject's body.

As used herein, the term "photobiomodulation therapy (PBMT)" refers to a drug-free, non-invasive treatment procedure, in which a light signal is applied to a certain region of a subject's body to treat a certain medical condition (e.g., pain, injury, disorder, disease, or the like) via a phototherapeutic response. In some instances, PBMT can be used alone to induce a phototherapeutic response, but in other instances, PBMT can be used in combination with medications and/or alternative therapies, like stress management or exercise, to achieve a more favorable treatment outcome.

As used herein, the term "light signal" refers to light having at least one wavelength. However, the light signal may include a combination of lights having wavelengths that create a synergistic effect when combined and improve the percentage of available light at greater tissue depths. In some instances, the wavelengths can be within a wavelength range of 600-1100 nm. For example, the wavelengths can include at least one wavelength corresponding to the visible range of the electromagnetic spectrum (e.g., red light) and at least one wavelength corresponding to the near-infrared or infrared range of the electromagnetic spectrum.

As used herein, the term "light source device" refers to a mechanical implement that can deliver a light signal of PMBT to a portion of the subject's body. Examples of the light source device include a probe, a flexible array device, or the like.

As used herein, the term "light source" refers to a component of a light source device that delivers one or more lights of different wavelengths. For example, the light source can be a low-level laser source (e.g., a laser light emitting diode (LED)) that generates coherent light. The low-level laser source can operate in a super pulsed mode that generates ultrashort pulses with a high peak power and minimal heat. As another example, the light source can be an incoherent light source, such as a traditional LED or light bulb. The incoherent light source can operate in a pulsed mode and/or a continuous mode.

As used herein, the term "phototherapeutic response" refers to a biological response to application of PBMT to a portion of the subject's body. The biological response can be reducing urinary incontinence by increasing conduction in one or more nerves associated with the bladder and/or bladder sphincter and/or increasing strength of one or more muscles associated with the bladder and/or bladder sphincter.

As used herein, the term "treatment" refers to medical care given to a subject to heal or cure a medical condition, like urinary incontinence. The terms "treatment" and "therapy" can be used interchangeably herein.

As used herein, the term "proximal" refers to a location that is near a target. For example, a device that is located proximal a patient's bladder can be located over the patient's bladder, but need not be directly over the center of the patient's bladder.

As used herein, the term "sufficient" refers to an amount adequate enough to satisfy a condition. For example, "a time sufficient to stimulate a phototherapeutic response" can refer to a light signal being applied to the patient's skin for a time adequate enough to stimulate the phototherapeutic response.

As used herein, the term "direct" refers to the absence of intervening elements. For example, a device that directly contacts a skin surface has no intervening elements between the device and the skin surface. When the term "contact" is used herein, it means "direct contact" unless otherwise stated.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

II. Overview

The present disclosure relates generally to urinary incontinence, which is due to the muscles and/or nerves of the bladder contracting and/or firing improperly. Traditional non-invasive therapies for urinary incontinence (like exercise training techniques, including pelvic floor muscle training and bladder training) are at best somewhat effective at treating the involuntary leakage characteristic of urinary incontinence, these non-invasive therapies do not work for every patient. More effective treatments, like surgery and electrical stimulation, are invasive and painful.

Photobiomodulation therapy (PBMT) provides a non-pharmacological therapy to patients suffering from urinary incontinence, including stress urinary incontinence and urge urinary incontinence. By applying PBMT to an area of the patient's skin proximal to the bladder in a transcutaneous and non-invasive manner, the PBMT can counteract the effects of urinary incontinence and lead to an improvement in overall quality of life. PBMT can be used to increase the strength of muscles proximal to the bladder (e.g., pelvic floor muscles and/or bladder muscles) and/or to regulate the firing of the nerves associated with the bladder. Advantageously, PBMT is more effective than traditional non-invasive therapies and less invasive than traditionally more effective treatments. Accordingly, the present disclosure relates, more specifically, to systems and methods treat urinary incontinence with PBMT. The PBMT can be applied discretely to eliminate patient embarrassment. Additionally, PBMT can be used in combination with exercise techniques (e.g., Pilates, Kegels, etc.) and/or other non-invasive therapies to increase effectiveness and manage the incidences of urinary incontinence.

III. Photobiomodulation Therapy (PBMT)

PBMT provides a non-pharmacological therapy that can be administered to a patient in a non-invasive manner to stimulate a phototherapeutic response. As used herein, a light signal is applied through the skin of a patient suffering urinary incontinence to an area proximal to the bladder, to stimulate a phototherapeutic response. In this case, the phototherapeutic response can include a biological response in nerves innervating muscles of the bladder wall and/or the muscles controlling the bladder sphincter and/or the bladder wall, which reduces urinary incontinence.

While not wishing to be bound by theory, there is strong evidence to suggest that one of the basic mechanisms of PBMT is the acceleration of electron transfer by electromagnetic radiation in the visible and near infrared region of the spectrum, via the modulation of cytochrome c-oxidase (CCO) activity. Traditionally, PBMT has attempted to modulate CCO activity using a single wavelength in the visible and near infrared region of the spectrum. However, the use of such single wavelengths cannot effectively modulate CCO activity since the single wavelength is limited by its specific absorption spectrum. The light signal used herein has a combination of wavelengths, which are used concurrently, providing an overlapping effect of peak activation, which accelerates CCO activity. Additionally, the time of CCO activation is prolonged across the entire therapeutic window by delivering much smaller doses across many wavelengths, rather than a single wavelength of a greater power. The multiple wavelengths enhance adenosine triphosphate (ATP) production, requiring less energy, and provides continual photodissociation of nitric oxide (NO), not only from CCO, but also from intracellular stores like nitrosylated forms of hemoglobin and myoglobin. NO is a potent vasodilator and PBMT can increase the vasodilation due to NO and increases the availability of oxygen to treated cells, and allows for greater traffic of immune cells into tissue.

Accordingly, in some instances, the light signal of the present disclosure includes a combination of individual light waves. The combination enhances each individual wavelength's ability to penetrate the skin, to allow for a greater portion of the available light energy to reach biological targets (nerves and/or muscles associated with the bladder) beneath the surface. Accordingly, the light signal can be configured so that individual light waves (from chosen light sources, with a selected wavelength, with a given power, and the like) within the light signal work constructively to create a synergistic effect. The light signal can be delivered by a light source device that includes a combination of one or more super pulsed lasers (which deliver a desired peak power from an ultrashort pulse with a minimized level of heat accumulated in the patient's tissue), one or more infrared emitting diodes, and one or more light emitting diodes. In some instances, the light source device can include groups of a super pulsed laser, an infrared emitting diode, and a light emitting diode. In other instances, the light source device can include groups of a super pulsed laser, at least three infrared emitting diodes, and at least three light source devices. The use of a super pulsed source can minimize the photo-thermal effect accumulating within the skin surface and target tissue. Additionally, the light source device can include a permanent magnet to provide a static (or constant) magnetic field.

IV. Systems

One aspect of the present disclosure can include a system 10 (FIG. 1) that applies photobiomodulation therapy (PBMT) to an area proximal to the bladder of a subject with urinary incontinence. In response to the PBMT, the nerves and/or muscles in the area proximal to the bladder (e.g., in the pelvic region on the ventral side of a patient's body) can undergo a phototherapeutic response, which can treat the urinary incontinence, improving the subject's overall quality of life. While PBMT is a non-pharmacological therapy that can be used alone to treat urinary incontinence, PBMT can also be used in combination with an alternative treatment (like exercise therapy, such as Pilates or Kegels) to treat urinary incontinence.

The system 10 can include at least a light source device 11 that delivers the PBMT to the area proximal to the bladder and a controller 12 to deliver inputs to the light source device 11 related to the delivery of the PBMT via a wired connection and/or a wireless connection. The PBMT can be applied to the area proximal to the bladder by a light signal that is generated by a light source device 11. To facilitate the delivery of the light signal to the area proximal to the bladder, the light source device 11 can be shaped so that at least a portion makes contact with the subject's skin in the area proximal to the bladder (e.g., the pelvic area and/or the lumbar area).

The light source device 11 can be configured in any shape that facilitates contacting a portion of the skin and/or the delivery of the light signal. An example of the light source device 11, including an electronics housing 2001 and a device housing 2002, is shown in FIG. 10. The electronics housing 2001 can include processing unit 14 and the power source and other electronics required for operation of the light source device 11. The device housing 2002 can surround the electronics housing and stabilize the electronics housing 2001. In some instances, the device housing 2002 can embody a securing mechanism to removeably secure the light source device 11 to an area of the subject's skin proximal to the patient's bladder. For example, the securing mechanism can be able to be disconnected to facilitate movement of the light source device 11. Even in the absence of the securing mechanism, the light source device 11 can be portable with at least a portion being able to be moved to different areas of the subject's body. For example, light delivery source clusters 13 can be within the electronics housing 2001 and/or within the device housing 2002.

Figure 5:
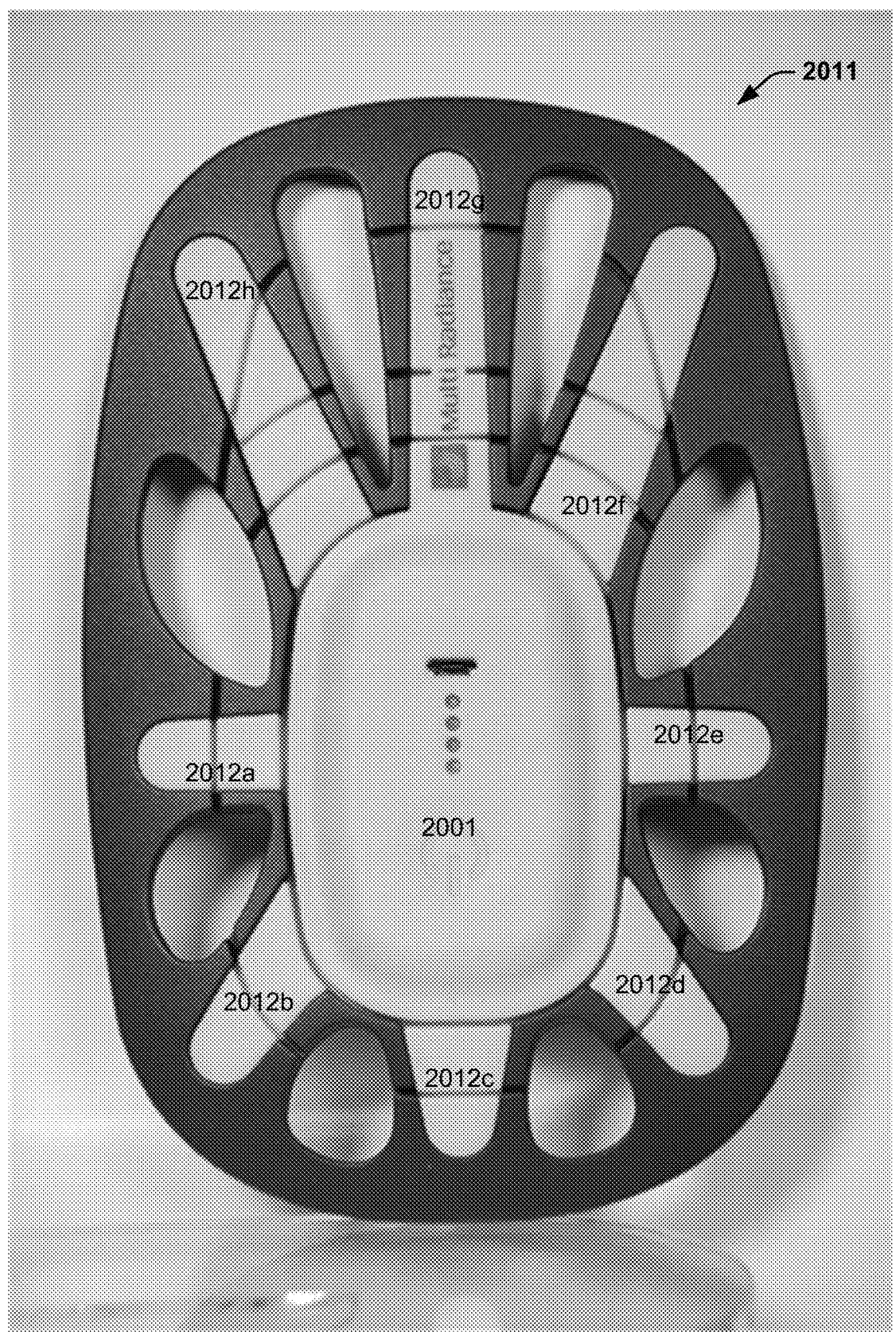

As one example, the light source device 11 can be embodied as an insert 2011 (shown in FIG. 5). The insert 2011 can include the electronics housing 2001 and a number of flanges 2012a-h extending from the device housing. Any number of flanges 2012a-h may exist, from 0 to N, where N is an integer limited only by the size of the insert. The electronics housing 2001 and/or the flanges can be made of a hard material (e.g., plastic) and/or a flexible material (e.g., silicone, rubber, neoprene, or the like) and configured with a shape or flexible into a shape that conforms to the patient's skin proximal to the bladder. The insert can be inserted into a device housing 2002. The device housing 2002 can be made of a flexible material (e.g., silicone, rubber, neoprene, or the like) and secured around an area of the subject's body that is proximal to the bladder (e.g., the pelvic region, the lumbar region, or the like).

Figure 6:

As another example, the light source device 11 can be embodied as a probe device 3011 (FIG. 6). The probe device 3011 can include a device housing 22 that is made of a hard material (e.g., a plastic) and include a portion configured to contact the subject's skin proximal to the bladder at a 90-degree angle to deliver the light signal. The electronics housing 2001 can be housed within the device housing 2002 with at least the light delivery source clusters 13 being included in an area that contacts the skin. Another example, although not illustrated, can include a flexible array device with a portion shaped to contact the skin at a 180-degree angle to deliver the light signal.

The light source device 11 can include at least one light delivery source to generate the light signal at a certain wavelength, with a certain power, in an operating mode. The operating mode can be at least one of a pulsed operating mode, a continuous operating mode, and a super-pulsed operating mode. The light source device 11 can also include a processing unit 14 programmed (e.g., preprogrammed, programmed in response to an input from the controller 12 (which may be in response to an input), or the like) with a time for application of the light signal to the area proximal to the bladder (e.g., the time can be sufficient to stimulate the phototherapeutic response in nerves and/or muscles related to the bladder). The processing unit 14 can also be programmed with the certain wavelength, the certain power, and/or the operating mode. In some instances, the light source device 11 can also include a permanent magnet to provide a static (or constant) magnetic field, which can be used to secure the light source device 11 to the area of the subject's skin and/or to affect the light signal. The constant magnetic field can be from 5 mT to 1 T (e.g., 35 mT). Additionally, the light source device 11 can also include a power source. The power source, in some instances, can be an internal battery. In other instances, the power source can receive and/or store power from an external source. In some instances, the external source can be associated with the controller 12.

In some instances, the light signal can include a light wave at a single wavelength of light delivered in a certain operating mode. However, in other instances, the light signal can include a combination of a plurality of individual light waves with different wavelengths of light delivered in two or more different operating modes. The combination of individual light waves is advantageous because the individual light waves can work constructively to create a synergistic effect, enhancing each individual wavelength's ability to penetrate the skin, allowing for a greater portion of the available light energy to reach biological targets beneath the surface of the skin.

Figure 2:
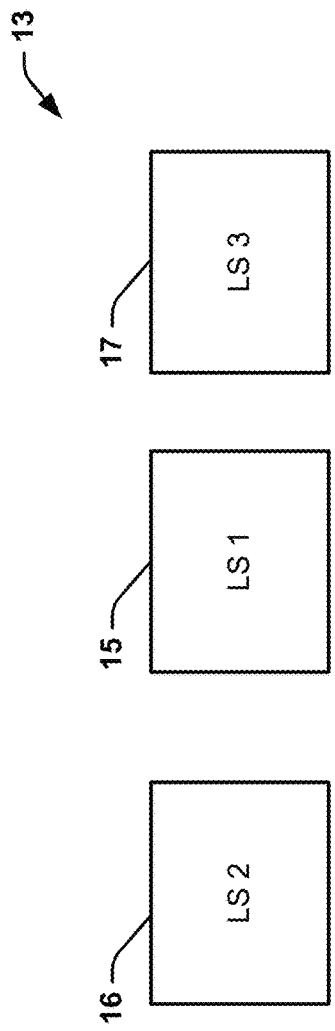
FIG. 2 is a block diagram illustration showing an example configuration of light sources within the light delivery source cluster of FIG. 1.

The plurality of individual light waves can be generated by a plurality of light delivery sources. Accordingly, the light source device 11 can include a plurality of light delivery sources, each configured to deliver light of a certain wavelength, with a given power, in a pulsed operating mode, a continuous operating mode, or a super-pulsed operating mode. One organization of the plurality of light delivery sources is in one or more light delivery source clusters 13 (an example of an individual cluster is shown in FIG. 2). In practice, the light source device can have any number of light delivery source clusters 13, limited only by the size of the area of the light source device 11 designated for delivery of the light signal.

As shown in FIG. 2, each light delivery source cluster 13 includes three types of light sources (LS1 15, LS2 16, LS3 17). However, the light delivery source clusters 13 may include a greater or fewer number of light sources. Three light sources are shown for simplicity of illustration and explanation. The light sources (LS1 15, LS2 16, LS3 17) each generate light waves with wavelengths within a wavelength range of 600-1100 nm (red to infrared). More particularly, LS1 15 can be configured to generate a first portion of the light signal with a wavelength from 890-910 nm (infrared); LS2 16 can be configured to generate a second portion of the light signal with a wavelength from 600-700 nm (red); and LS3 17 can be configured to generate a third portion of the light signal with a wavelength from 810-880 nm. In this example, LS1 15, which is in the middle of each light delivery source cluster 13, can operate in the super-pulsed operating mode, while LS2 16 and LS3 17, which surround LS1, can each operate in the continuous operating mode or the pulsed operating mode. In other words, LS1 can be a super pulsed laser that creates an impulse of high intensity that emits for a billionth of a second in synchrony with LS2 (a red source, like a red LED or a red light) and/or LS3 (an infrared source, like an infrared LED or an infrared light). As a more specific example, LS1 can be a super pulsed light source generating 905 nm light, while LS2 and LS3 can generate continuous and/or pulsed light at 850 nm wavelength (infrared light) and 630 nm (red light) wavelength, respectively. Advantageously, the use of the super-pulsed laser (LS1) allows a desired peak power to be delivered for an ultrashort pulse with a minimized level of heat accumulated in the subject's skin and (in other words, minimizes the photothermal effect).

Many configurations of each light delivery source cluster 13 are possible. Two examples of possible configurations are set forth, but countless other possibilities exist (including with other light sources), as long as there are one or more LS1, one or more LS2, one or more LS3. One possible configuration of each light delivery source cluster 13 is a 1:1:1 configuration, with LS1 (the super-pulsed laser) between LS2 (the red source) and LS3 (the infrared source). Another possible configuration of each light delivery source cluster 13 is a 1:3:3 configuration with LS1 surrounded by three (or more) LS2 and three (or more) LS3. For example, in this configuration, LS2 and LS3 can alternate as they are arranged around LS1 (e.g., LS2 LS3 LS2 LS3 LS2 LS3 surrounding LS1). As another example, LS2 and LS3 can be grouped together around LS1 (e.g., LS2 LS2 LS2 LS3 LS3 LS3). Although not expressly described, other example configurations are possible in the 1:3:3 light delivery source cluster 13. The light delivery source clusters 13 within the same light source device 11 can be configured identically, but need not have identical configurations. For example, a light source device 11 can have three light delivery source clusters, with one a 1:1:1 configuration and the other two 1:3:3 configurations.

As an example, the parameters can be 1 superpulsed laser at 50 W, 3 infrared emitting diodes at 250 mW, and 3 red LEDs at 200 mW (however, these powers can be different), and a static magnetic ring of 35 mT. The frequencies can change for stress urinary incontinence and urge-based urinary incontinence.

V. Methods

Another aspect of the present disclosure can include a method 30 (FIG. 3) for applying photobiomodulation therapy (PBMT) to an area proximal to a bladder of a subject who experiences urinary incontinence to treat the urinary incontinence. The method 30 can be executed by hardware—for example, at least a portion of the system 10 shown in FIG. 1 and described above. Additionally, PBMT provides a non-pharmacological therapy to patients suffering from urinary incontinence, which can be used alone or in combination with an alternative treatment (like exercise therapy—Pilates, Kegels, or the like) to treat urinary incontinence.

The method 30 is illustrated as process flow diagrams with flowchart illustrations. For purposes of simplicity, the method 30 is shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the method 30. Additionally, one or more elements that implement the method 30, such as light source device 11 and/or controller 12 of FIG. 1, may include a non-transitory memory and one or more processors that can facilitate the configuration and generation of the light signal.

Figure 3:
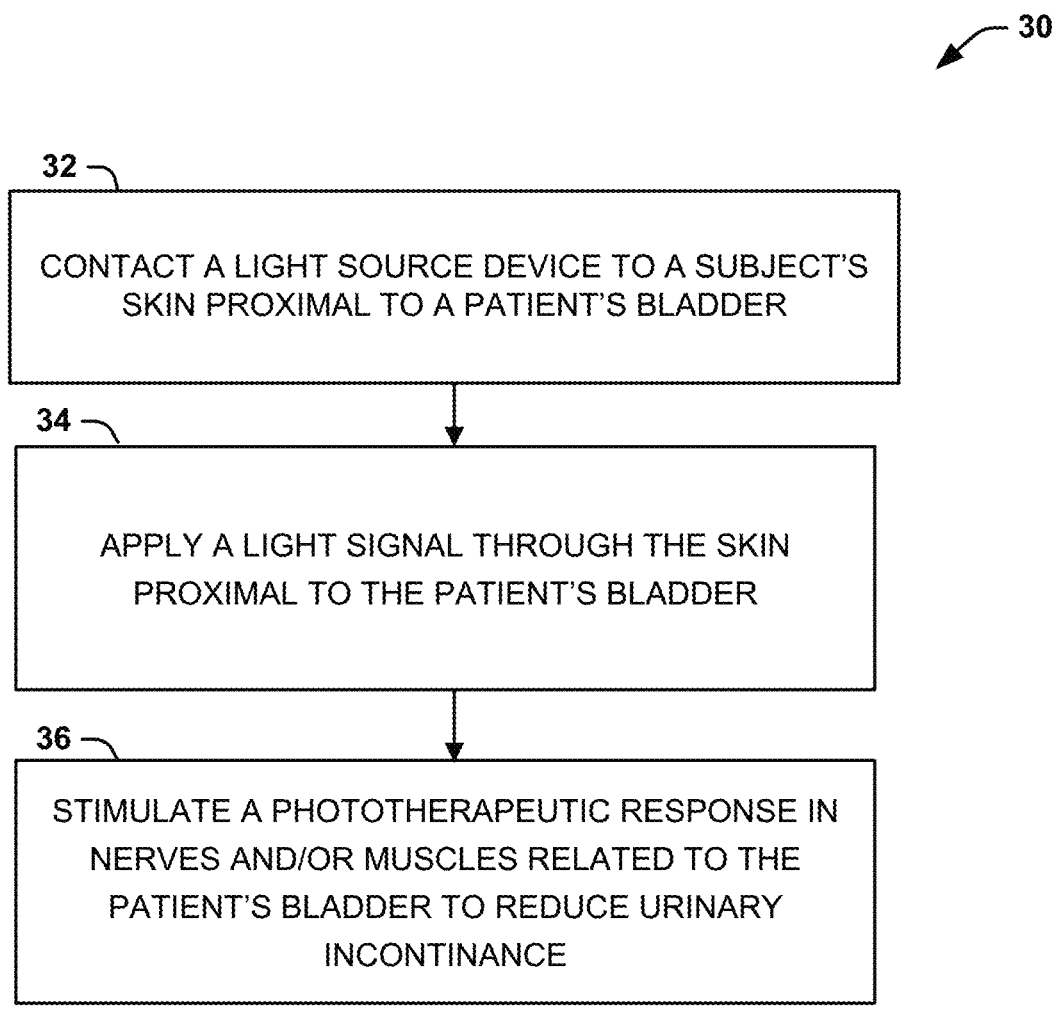
FIG. 3 is a process flow diagram of an example method for applying PBMT to the area proximal to a subject's bladder in accordance with another aspect of the present disclosure.
Figure 4:
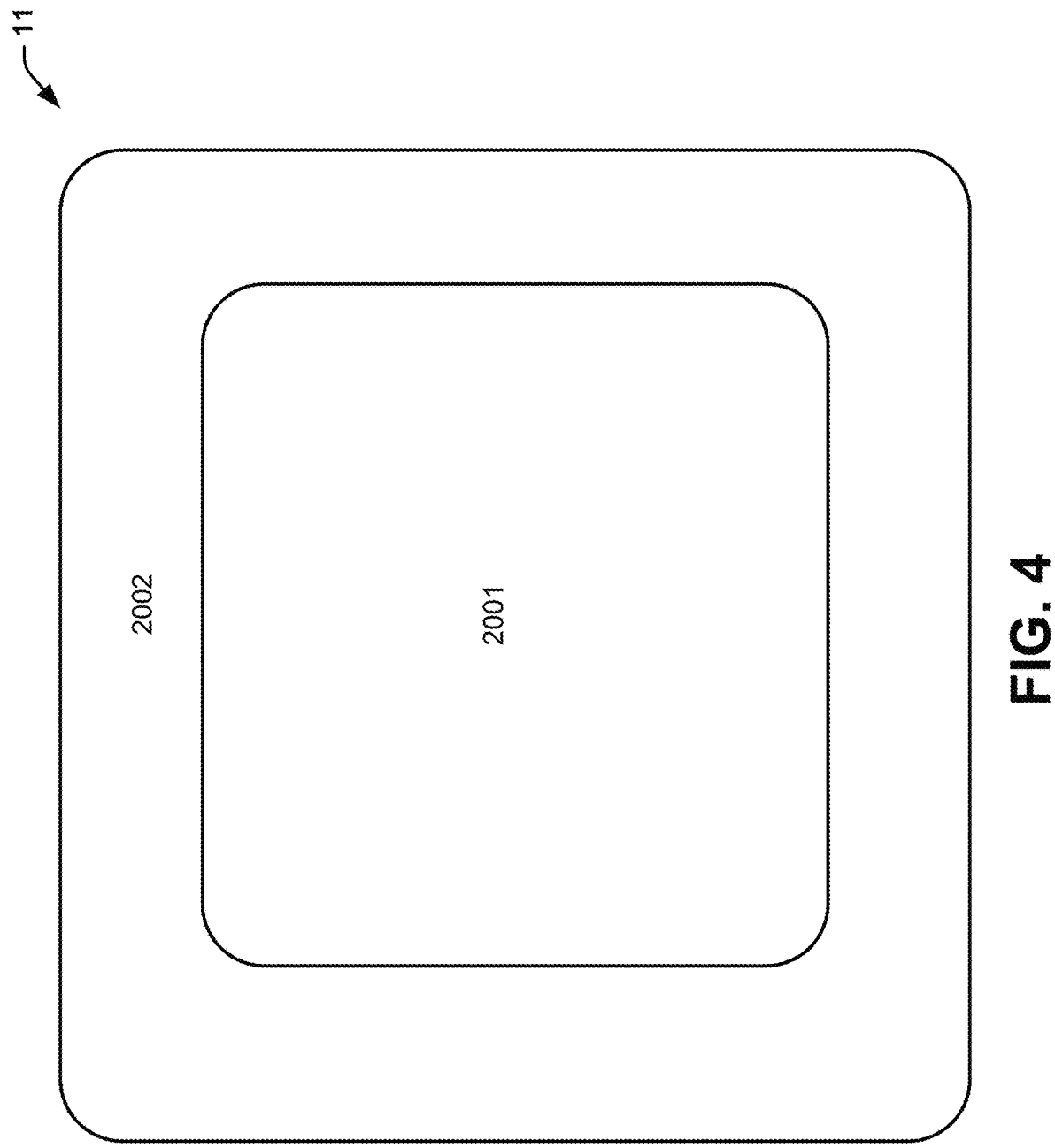
FIGS. 4-6 are example implementations of at least a portion of the system of FIG. 1.

Referring now to FIG. 3, illustrated is a method 30 for applying PBMT to an area proximal to the bladder (to stimulate nerves and/or muscles associated with the bladder) to treat urinary incontinence. At step 32, a light source device (e.g. light source device 11) can be contacted to a subject's skin proximal to (e.g., directly adjacent or over) the bladder. For example, the light source device can be contacted to the skin in the pelvic region and/or the lumbar region of the patient's body. At step 34, a light signal can be applied through the skin proximal to the patient's bladder. The light signal can be generated in at least one of a pulsed operating mode, a continuous operating mode, and a super-pulsed operating mode. The light signal can include one wave of a single wavelength. However, alternatively, the light signal can include a plurality of individual waves with multiple wavelengths. The combination of the plurality of individual waves can work constructively to create a synergistic effect, enhancing each individual wavelength's ability to penetrate the skin, allowing for a greater portion of the available light energy to reach biological targets beneath the surface of the skin. The light signal is applied for a time sufficient to stimulate a phototherapeutic response. At step 36, a phototherapeutic response can be stimulated in the nerves and/or muscles related to the bladder to reduce urinary incontinence, leading to an improvement in a subject's overall quality of life

VI. Experimental

The following examples are shown for the purpose of illustration only and are not intended to limit the scope of the appended claims. These experiments demonstrate the promise of photobiomodulation therapy (PBMT) as a non-pharmacological tool for treating stress urinary incontinence. The PBMT provides a non-pharmacological treatment that does not present harmful side effects, making PBMT a promising tool for treating stress urinary incontinence. Additionally, PBMT can be combined with exercise training (EXT), like pelvic floor muscle training and bladder training, to further reduce pain and improve health-related quality of life as well as functional capacity.

Stress Urinary Incontinence is defined as the involuntary loss of urine through the external urethral ostium, secondary to increased abdominal pressure in the absence of detrusor contraction. The Pilates Method aims at the control and awareness of body movement. This long-term clinical research Example evaluated whether the Pilates method associated with low intensity laser therapy is effective in the treatment of stress urinary incontinence in women.

Methods

Characterization and Purpose of the Study

The present study was a randomized, double-blind, placebo-controlled clinical study conducted by the Physiotherapy Department of University Center Cenecista of Bento Goncalves (UNICNEC), in the city of Bento Goncalves, Brazil. The study was approved by the Ethics Committee of the UNICNEC, in accordance with the Declaration of Helsinki, all subjects were instructed on the procedure and signed a free and informed consent form before participating in the study (CAEE 52341315.1.0000.5571). This study was registered in the Brazilian Clinical Trials Registry (REBEC).

Volunteers were randomly allocated to three groups (n=11 per group), based on three interventionist groups with pilates/placebo (PPG), pilates/PBMT/sMf (PPActG), and PBMT/sMf alone (PG). Randomization will be carried out through a simple draw (A, B, C or D) by a blind researcher (without knowledge of the interventions that each group will receive). Another researcher responsible for applying the PBM/sMF received the batches after randomization and will determine which group will perform the PPG, PPActG and PG. Only the researcher responsible for applying the PBMT/sMF was aware of the interventions in each group.

Evaluations and Informative Procedures

Evaluation consisted of anamnesis and physical examination, evaluation of muscle strength (Oxford Scale), completion of the ICIQ-SF questionnaire (International Consultation on Incontinence Questionnaire—Abbreviated form) and measurement of urinary loss Pad test. The evaluation of muscle strength and filling in the ICIQ-SF questionnaire were performed on the first and last days, while the Pad test was applied on days 01, 09, 17 and 24 of intervention. All evaluation methods were conducted by a blind evaluator regarding randomization. The volunteers were informed about the procedures and signed a declaration of informed consent, according to Resolution 196/96 of the National Health Council of Brazil, before the study was carried out.

Personal Data and Anamnesis

A questionnaire included age (years), body mass (kilograms), height (centimeters), dominant leg, education level (without education, elementary school, high school, some college, or higher) and marital status (single, married or widowed), Main complaint, history of disease and family history.

Muscle Strength

For the evaluation of the muscular strength of the pelvic floor muscles, the participant was positioned in the supine position, with flexed hips and slight abduction. Initially, in the perineal contraction, the force of contraction of the pelvic floor muscles was verified, through the digital palpation of the MAP, according to the Modified Oxford Scale. MAP strength is graded from zero (when no contraction is noticeable) to five (when the examiner's fingers are compressed and elevated).

Muscle Tone

The assessment of MAP tonicity was performed through bi/digital palpation, according to the Puborectal muscle tone assessment scale (Dietz, 2008), which is an ordinal scale, from 0 to 5 points. Following the recommendation of the ICS, the tone was graded as low (Grade 0 to 2 Dietz), Normal (Grade 3 Dietz) or High (Grade 4 and 5 Dietz).

International Consultation on Incontinence Questionnaire

The International Consultation on Incontinence Questionnaire (ICIQ) was given to each of the subjects. The ICIQ-SF is a questionnaire used to assess urinary incontinence composed of six questions that assess the frequency, severity of urinary loss and the impact of urinary incontinence on daily life, in addition to a sequence of eight self-diagnosis items, related to the causes or incontinence situations that are not scored. The sum of the scores of questions three, four and five varies from 0 to 21, and the higher the total score, the greater the severity of urinary incontinence. The impact of daily life is defined according to the score of question five; (0) nothing, (1-3) mild, (4-6) moderate, (7-9) severe and (10) very severe.

Urinary Loss

The 1-hour Pad Test, standardized and validated 1988 by the International Continence Society (ICS) is a simple, non-invasive and effective method to objectively assess urinary loss. To perform the test, the participant was instructed to ingest half a liter of water and to wear a previously weighed absorbent. After thirty minutes have elapsed after the water was ingested, the participant was instructed to walk, climb and go down stairs and ramps for ten minutes; sit and get up from a chair ten times; cough vigorously ten times; run in place for a minute; crouch to pick up an object on the floor five times and wash hands under running water for one minute. After the one hour period elapsed, the absorbent was removed and weighed again.

Photobiomodulation Therapy Combined with Static Magnetic Field (PBM/sMF)

The PBM/sMF therapy will be used pre-exercise in all sessions, the emitter equipment used was the portable model MR5-ACTIVET PRO Laser Shower, Multi Radiance Medical® (Solon, Ohio, USA).

For stress urinary incontinence, for the experimental group, PBMT was applied to the pelvic region on the ventral side of the patient's body at a 60 J dose to small muscle groups at 250 Hz. a 60 J dose to small muscle groups at 250 Hz. The device had 1 super pulsed laser at 50 W and 905 nm, 3 RED LEDs at 250 mW and 850 nm, and 3 LEDs (red) at 200 mW and 630 nm. In some instances, the device can also have a static magnetic ring at 35 T.

The cluster will be applied in direct contact with the skin stationary with an angle of 90° and a little pressure, in the regions of the mount of the pubis and in the region of the perineum.

Experimental procedures are shown in Table 1 and Table 2.

TABLE 1

Experimental Procedures.

| | Quantity IR | Quantity SPL | PI, SPL, W | TI, ns | Apperture, cm2 | Pav *-SPL, mW | Pav-IR, mW | Pav-Red, mW |
|---|---|---|---|---|---|---|---|---|
| 1 SE25 | 3 | 1 | 50 | 100 | 4 | 1.25 | 250 | 200 |
| 2 Shower Round | 8 | 4 | 50 | 100 | 20 | 1.25 | 70 | 60 |
| 3 Shower Rect | 4 | 6 | 50 | 100 | 25 | 1.25 | 70 | 60 |
| 4 Stim | 4 | 1 | 25 | 100 | 4 | 0.625 | 70 | 60 |

TABLE 2

Experimental Procedures (continued), time 120 s

| Emitter # 1 | 2.19E−19 SPL | 2.27E−19 IR | 2.96E−19 Red | J/photon Total |
|---|---|---|---|---|
| Photons/sec | 5.15E+15 | 1.10E+18 | 6.75E+17 | 1.78E+18 |
| Irrad, W/cm2 | 0.00241 | 0.0625 | 0.05 | 1.15E−01 |
| Energy, J | 0.15 | 30 | 24 | 5.42E+01 |
| Fluence, J/cm2 | 0.340909 | 7.5 | 6 | 1.38E+01 |

Training Session

Pilates Method exercises were performed on the ground based on the Elliworth 22 protocol lasting 50 minutes and six repetitions for each movement performed. The participants were instructed to perform a contraction of the pelvic floor muscles, associated with contraction of the transverse abdomen muscle during the proposed exercises. The protocol was initially composed of: Heating: 20 Breaths (inhale/exhale/center/contract); Strengthening: Double Leg, Single Leg Stretch, Leg circles, Hip lift on the ball, Abdominal strengthening on the ball, Alternation of two supports, Side flexion, Side Kick-kick, Side Kicks, Shell; Stretching: Swan—anterior chain, Neck Pull—posterior chain, held for 1 minute. These exercises were performed until the eighth session.

After that, there was an evolution in the exercise protocol, also lasting 50 min and six repetitions, as follows: Warm-up: 20 Breaths (inhale/exhale/center/contract); Strengthening: The Saw, Swan Dive, Book close series, Hip lift on the ball, Leg circles, Alternation of two supports, Lateral Flexion, Side Kick-kick, Side Kicks, Shell; Stretches: Swan—anterior chain, Neck Pull—posterior chain, maintained for 1 minute. These exercises were performed until the sixteenth session.

In the seventeenth session there was a new evolution in the exercises, with 50 minutes and six repetitions each, consisting of: Warm-up: 20 Breaths (inhale/exhale/center/contract); Strengthening: Double Leg Stretch, Book Close series, Swimming, Swan Dive, Leg Pull Front, Alternation of two supports, Side flexion, Side Kick-side kick, Side Kicks, Shell; Stretches: Swan—anterior chain, Neck Pull—posterior chain, held for one minute. Until the twenty-fourth and last session, where all the evaluation processes were carried out again as previously described.

Data Analysis

Data are expressed as mean and SD in text and as mean and SEM in the figures. To analyze data, evaluation of muscle strength and filling in the ICIQ-SF questionnaire were performed on the first and last days, while the Pad test was applied on days 01, 09, 17 and 24 of intervention. The values obtained for each variable will undergo the Shapiro-Wilk normality test. Based on randomization, variables were compared using t test (time on pitch and distance covered) and analysis of variance, with repeated measurements for the factors of time of collections, as well as testing between-and within-group differences (followed by a post hoc Bonferroni test). The SPSS 20.0 software was used for the statistical analysis, with a significance level of 5% ($p<0.05$). Magnitude-based inference analyses were also used to examine practical significances. The magnitude of differences (Cohen-d) between groups was calculated using the mean and SD of placebo and PBMT treatments (using Gpower 3.1). We adopted the criteria of Cohen for the analysis (0.2: small; 0.50: moderate; 0.80: large).

Results

The Experiment showed that the addition of PBMT works to stop stress incontinence more than the Pilates exercise alone. It should be noted that the PBMT also works for urge-based incontinence with a different dose of 100 Hz for 5 minutes to the same location of the lumbar spine.

Figure 7:
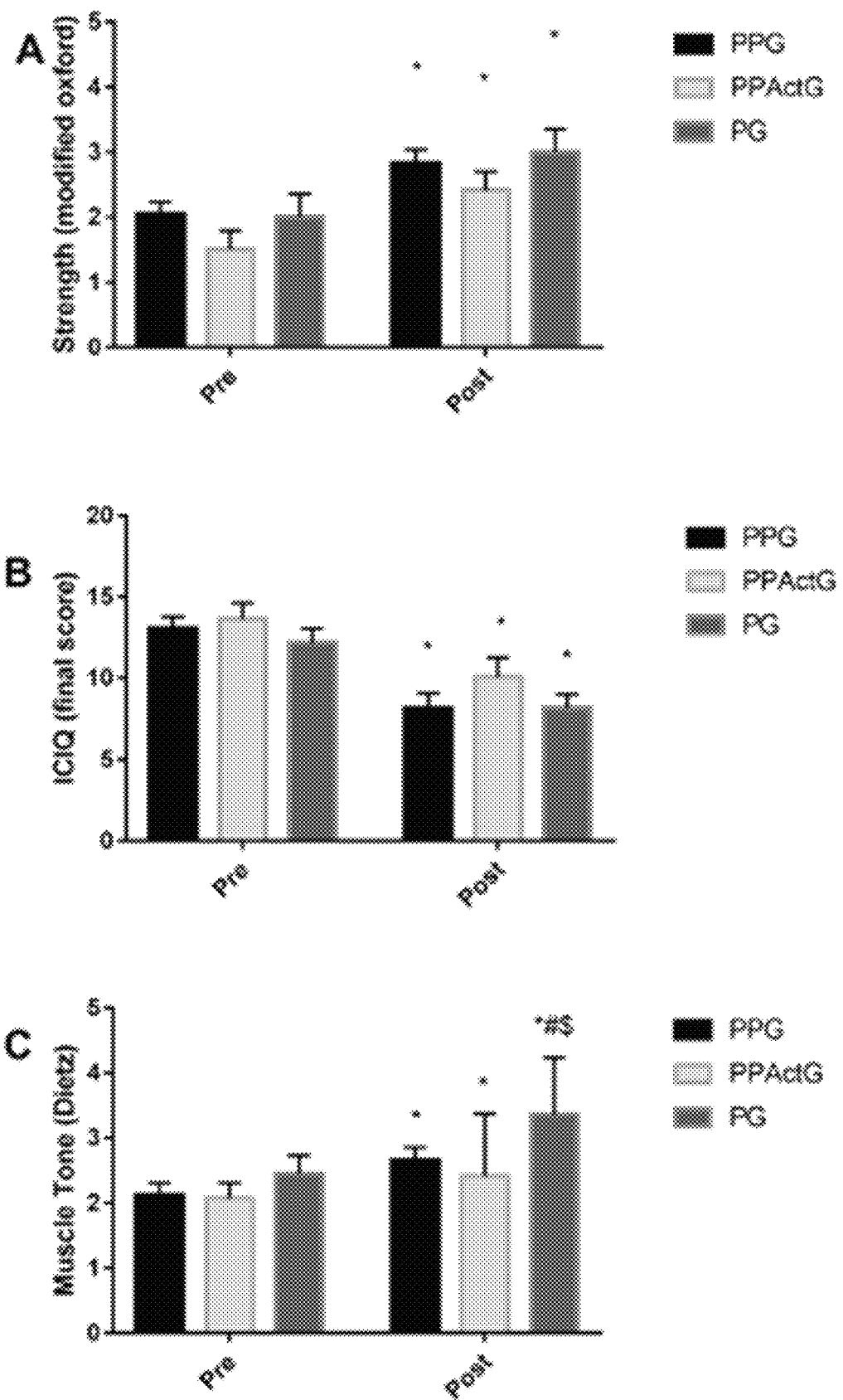
FIG. 7 shows comparisons between each of strength (A), International Consultation on Incontinence Questionnaire (ICIQ) (B), and muscle tone (C) for pilates/placebo (PPG), pilates/PBMT/sMf (PPActG), and PBMT/sMf alone (PG).

Forty-six women with stress urinary incontinence participated in this study. The mean age was 50.74±8.80 years. The evaluation conditions (pre) for all variables did not show a statistically significant difference. The only statistically significant differences ($p<0.05$) between the groups were observed in the tonus variable, where the GP group showed a higher mean in the post measure when compared to the other groups (FIG. 7). In the comparisons of urinary loss, strength, tone and intra-group ICIQ, statistically significant differences can be observed (Table 3, FIG. 7). In FIG. 7, elements A, B *Statistically significant difference in comparison with the pre ($p<0.01$); element C *Statistically significant difference in comparison with the pre ($p<0.01$), #Statistically significant difference in comparison with the Post PPG (p=0.02), $ Statistically significant difference in comparison with the Post PPActG (p=0.01).

The results of the strength analysis (FIG. 7, element A), a statistically significant difference (p<0.01) was found between the pre collection (2.04±0.92 PPG; 1.5±1.0 PPActG; 2±1.18 PG) and post (2.82±1.02 PPG; 2.41±0.99 PPActG; 3.0±1.18). Considering the pre-condition as 100%, we have a strength increase of 38.29% for PPG, 61.1% PPActG and 50.0% for PG. For the results referring to the ICIQ (FIG. 7, element B), a statistically significant difference (p<0.01) was found between the pre collection (13.04±3.53 PPG; 13.66±3.3 PPActG; 12, 18±2.89 PG) and post (8.13±4.49 PPG; 10.08±4.07 PPActG; 8.18±2.75). Considering the precondition as 100%, we have an improvement in the quality of life of 62.3% for PPG, 73.7% PPActG and 67.1% for PG.

Regarding the results related to tone (FIG. 7, element C), a statistically significant difference (p<0.01) was found between the pre collection (2.13±0.86 PPG; 2.08±0.99 PPActG; 2.45±0.68 PG) and post (2.65±0.98 PPG; 2.41±0.79 PPActG; 3.36±0.92), as well as observing a statistically significant difference when comparing the post means of the groups (PG×PPG p=0.02; PG×PPActG p=0.01). Considering the pre-condition as 100%, we have a 24.4% tonus increase for PPG, 16.0% PPActG and 37.0% for PG.

A decrease in urinary loss was observed by analyzing the results of the Pad Test (Table 3) and considering the pre-condition as 100%, we have a variation of 49.9%, 34.22%, 25.17% in evaluations 4 weeks, 8 weeks and 12 weeks for PPG, 58.84%, 40.77%, 25.20% for 4 weeks, 8 weeks and 12 weeks for PPActG evaluations and 42.31%, 35.46%, 24.72% for ratings 4 weeks, 8 weeks and 12 weeks for the for PG.

TABLE 3

| Lost Urine (g), Results of Pad Test | | | | |
|---|---|---|---|---|
| Group | Pre | Post 4 weeks | Post 8 weeks | Post 12 weeks |
| PPG | 1.28 ± 0.93 | 0.64 ± 0.71* | 0.43 ± 0.62* | 0.32 ± 0.32* |
| PPActG | 1.46 ± 0.74 | 0.86 ± 0.40* | 0.59 ± 0.43*# | 0.36 ± 0.36*#$ |
| PG | 1.34 ± 0.60 | 0.56 ± 0.48* | 0.47 ± 0.58* | 0.33 ± 0.33* |

Mean ± Standard Deviation;
*difference to the pre (p < 0.01);
difference to the post 4 weeks (p < 0.01);
$difference to the post 8 weeks (p < 0.01).

From the above description, those skilled in the art will perceive improvements, changes and modifications. Such improvements, changes and modifications are within the skill of one in the art and are intended to be covered by the appended claims.

What is claimed is:

1. A method comprising:
   contacting a light source device to a subject's skin proximal to a subject's bladder; and
   applying a light signal through the light source device to the subject's skin proximal to the subject's bladder,
   wherein the light signal is applied for a time sufficient to stimulate a phototherapeutic response in one or more muscles proximal to the bladder to treat urinary incontinence,
   wherein the light source device comprises at least three light sources each configured to apply a portion of the light signal,
   wherein the at least three light sources comprise a first source configured to generate a first portion of the light signal with a wavelength from 890-910 nm, a second source configured to generate a second portion of the light signal with a wavelength from 600-700 nm, and a third source configured to generate a third portion of the light signal with a wavelength from 810-880 nm,
   wherein the first light source operates in the super-pulsed operating mode, the second light source operates in the pulsed operating mode or the continuous operating mode, and the third light source operates in the pulsed operating mode or the continuous operating mode, and
   wherein the first light source comprises a super pulsed laser that creates an impulse of high intensity that emits for a billionth of a second in synchrony with the third light source.

2. The method of claim 1, wherein the light source device is a probe device or a flexible array device.

3. The method of claim 1, wherein the subject performs an exercise to strengthen the one or more muscles proximal to the bladder adjunctive to application of the light signal.

4. The method of claim 1, wherein the first light source comprises a super-pulsed infrared laser source, the second light source comprises a red light source, and the third light source comprises an infrared light source.

5. The method of claim 4, wherein the second light source further comprises at least three red light sources and the third light source further comprises at least three infrared light sources.

6. The method of claim 1, wherein the light source device further comprises a static magnetic ring that provides a constant magnetic field.

7. The method of claim 6, wherein the constant magnetic field is from 5 mT to 1 T.

8. The method of claim 1, wherein the light source device is a portable device comprising a power source.

9. The method of claim 1, wherein the light source device is removeably secured to the area of the subject's skin.

10. The method of claim 1, wherein the light source device is contacted to the subject's skin to apply the light signal to a dorsal or ventral portion of the subject's body at a lumbar spinal region or a pubic region.

11. A light source device configured to contact a subject's skin proximal to a subject's bladder comprising:
    at least three light sources each configured to apply a portion of the light signal comprising a different wavelength within a wavelength through the light source device to the subject's skin proximal to the subject's bladder,
    wherein the at least three sources comprise a first source configured to generate a first portion of the light signal with a wavelength from 890-910 nm, a second source configured to generate a second portion of the light signal with a wavelength from 600-700 nm, and a third source configured to generate a third portion of the light signal with a wavelength from 810-880 nm,
    wherein the first light source operates in the super-pulsed operating mode, the second light source operates in the pulsed operating mode or the continuous operating mode, and the third light source operates in the pulsed operating mode or the continuous operating mode, and
    wherein the first light source comprises a super pulsed laser that creates an impulse of high intensity that emits for a billionth of a second in synchrony with the third light source;
    a processing unit preprogrammed with a time of application of the first pulsed light, the second pulsed light, and the third light signal, wherein the time of application is sufficient to stimulate a phototherapeutic response in one or more muscles proximal to the bladder to treat urinary incontinence; and a power source.

12. The light source device of claim 11, further comprising a permanent magnet that provides a constant magnetic field from 5 mT to 1 T.

13. The light source device of claim 11, wherein the first light source comprises a super-pulsed infrared laser source, the second light source comprises at least one red light source, and the third light source comprises at least one infrared light source.

14. The light source device of claim 11, wherein the at least three light sources are components of a probe device or a flexible array device.

15. The light source device of claim 11, further comprising a securing mechanism to removeably secure at least the at least three light sources to the subject's skin proximal to the subject's bladder.

* * * * *